United States Patent [19]
Kadhiresan et al.

[11] Patent Number: 6,135,970
[45] Date of Patent: Oct. 24, 2000

[54] METHOD AND APPARATUS FOR ASSESSING PATIENT WELL-BEING

[75] Inventors: V. A. Kadhiresan, Lino Lakes; Julio C. Spinelli, Shoreview, both of Minn.

[73] Assignee: Cardiac Pacemakers, Inc., St. Paul, Minn.

[21] Appl. No.: 09/456,767

[22] Filed: Dec. 7, 1999

Related U.S. Application Data

[63] Continuation of application No. 09/344,668, Jun. 25, 1999, Pat. No. 6,021,351, which is a continuation-in-part of application No. 09/076,025, Jun. 16, 1999.

[51] Int. Cl.[7] ................................................. A61B 5/103
[52] U.S. Cl. ............................................................ 600/595
[58] Field of Search ................................ 600/510, 587, 600/595

[56] References Cited

U.S. PATENT DOCUMENTS

| | | | |
|---|---|---|---|
| 4,117,834 | 10/1978 | McPartland et al. | 600/595 |
| 4,353,375 | 10/1982 | Colburn et al. | 600/595 |
| 4,608,998 | 9/1986 | Murdock | 600/595 |

OTHER PUBLICATIONS

Vera Bittner, M.D., et al. "Prediction of Mortality and Morbidity With a 6–Minute Walk Test in Patients With Left Ventricular Dysfunction", *Journal of the American Medical Association*, Oct. 13, 1993, vol. 270, No. 14, pp. 1702–1707.

Nancy P. Milligan, et al. "Using a 6–Minute Walk Test to Predict Outcomes in Patients with Left Ventricular Dysfunction", *Rehabilitation Nursing*, Jul./Aug. 1997, vol. 22, No. 4, pp. 177–181.

Carlijn V.C. Bouten, et al. "A Triaxial Accelerometer and Portable Data Processing Unit for the Assessment of Daily Physical Activity", *IEEE Transactions On Biomedical Engineering*, Mar. 1997, vol. 44, No., pp. 136–147.

Nicolas Delahayne, M.D., et al. "Comparison of Left Ventricular Responses to the Six–Minute Walk Test, Stair Climbing, and Maximal Upright Bicycle Exercise in Patients With Congestive Heart Failure Due to Idiopathic Dilated Cardiomyopathy", *The American Journal of Cardiology*, Jul. 1, 1997, vol. 80, pp. 70.

John T. Walsh, et al. "Relation of Daily Activity Levels in Patients with Chronic Heart Failure to Long–Term Prognosis", *The American Journal of Cardiology*, May 15, 1997, vol. 79, pp. 1364–1369.

*Primary Examiner*—William E. Kamm
*Attorney, Agent, or Firm*—Nikolai, Mersereau & Dietz, P.A.

[57] ABSTRACT

An apparatus and method for assessing the status of well-being of patients being treated for CHF using cardiac pacing as a therapy. By sampling the output from an activity sensor or the like, and by noting the frequency with which the averaged rectified sensor output exceeds a preset threshold following changes in the pacing mode, the efficacy of the new mode compared to the previous one can be evaluated.

13 Claims, 6 Drawing Sheets

METHOD AND APPARATUS FOR ASSESSING PATIENT WELL-BEING

This is a Continuation of copending application Ser. No. 09/344,668, filed Jun. 25,1999, now U.S. Pat. No. 6,021,351 which is a Divisional of copending application Ser. No. 09/076,025, filed Jun. 16, 1999.

BACKGROUND OF THE INVENTION

I. Field of the Invention

This invention relates generally to an apparatus and method for assessing effectiveness of changes in therapy on a patient's wellbeing, and more particularly to the long-term assessment of changes in the mode of pacing of CHF patients on their ability to carry out routine daily activities.

II. Discussion of the Prior Art

When cardiac pacemakers were first introduced, they were used primarily to pace the heart when the normal conduction path from the heart's sinoatrial node to its atrial ventricular node or from the atrial ventricular node to the ventricles was interrupted. The pacemaker was called upon to deliver ventricular stimulating pulses to maintain a predetermined heart beat rate. More recently, pacing has been used to enhance the hemodynamic performance of the heart in patients suffering from congestive heart failure (CHF) or other type of left ventricular dysfunction. It has been found that by pacing the left ventricle and appropriately setting the AV delay parameter of a pacemaker, the patient's cardiac output can be optimized.

To assess the efficacy of changes made in a pacing parameter such as pacing rate or A-V delay interval, it is of interest to monitor the level of activity of the patient over prolonged periods of time in that it is now well recognized that the activity profile of CHF patients is indicative of their well being and prognosis. That is to say, a direct correlation has been found between a CHF patient's level of activity and their overall well-being. Currently, exercise tests and quality of life questionnaires administered at the physician's office determine the patient's status. It is desirable, however, to determine the status of the patient in a natural setting. Among the many exercise tests that have been employed by physicians in assessing the long-term prognosis of CHF patients has been the "six-minute walk" distance. In a paper entitled "Prediction of Mortality and Morbidity with a Six-Minute Walk Test in Patients with Left Ventricular Dysfunction" by Vera Bittner, M. D., et al. and published in the Oct. 13, 1993 edition of the *Journal of the American Medical Association* (Vol. 240, No. 14, pp. 1702–1707) a study is described that was performed to determine the potential usefulness of the six-minute walk test as a prognostic indicator in patients with CHF. Based on the distances that the several patients included in the test were able to achieve during a six-minute walk at submaximal effort levels, a definite correlation was found, with the distance walked being inversely related to patient mortality and morbidity. See FIGS. 1 and 2. A similar study with similar outcomes is described in a paper entitled "Using a Six-Minute Walk Test to Predict Outcomes in Patients with Left Ventricular Dysfunction" by Nancy P. Milligan, R. N. et al., published in the July/August 1997 edition of *Rehabilitation Nursing* (Vol. 22, No. 4, pp. 177–181).

The six-minute walk test is generally carried out under closely controlled conditions in a hospital or clinic. Patients are asked to walk up and down a corridor at their own rate as a medical professional times and calculates the distances traversed in a six-minute period. A pedometer affixed to the patient's leg may be used to determine the distance traversed, but usually the distance is determined from the length of the corridor and the number of times the patient has walked it in a six-minute interval.

Activity can also be measured by means of an accelerometer affixed to the patient. As is pointed out in an article by C.V.C. Bouten et al. entitled a "Triaxial Accelerometer and Portable Data Processing Unit for the Assessment of Daily Physical Activity", published in the *IEEE Transactions on Biomedical Engineerinq*, Vol. 44, No. 3, March 1997, pp. 136–147, information derived from a patient-worn accelerometer can reliably be used for the assessment of that patient's physical activity and it offers the advantage that the information may be gathered in the course of more normal patient activities. Studies we have conducted show a direct, positive correlation between the frequency with which the output from a patientworn accelerometer exceeds a predetermined threshold and the distance traversed during a six-minute walk test protocol. Therefore, we are able to conclude that accelerometer-derived data can be used in assessing patient well-being and we have developed an apparatus and algorithm using an activity sensor to assess the efficacy of a change in pacing therapy on that patient's overall well-being.

SUMMARY OF THE INVENTION

As mentioned, the present invention provides apparatus and a method of using same for determining whether a change in a mode of pacing a CHF patient enhances or decreases that patient's overall well-being. It can also be used to assess efficacy of different rate responsive algorithms for rate responsive pacemakers. The method involves the steps of affixing to the patient one or more sensors capable of sensing a parameter related to the patient's level of activity and for providing an electrical output signal(s) corresponding to such activity level. A monitoring protocol is established which defines (1) a total time period in which the assessment is to be accomplished, (2) a plurality of first time periods in which different pacing modes are employed in each, and (3) the number of instances within each of the plurality of time periods that the sensor output signals are sampled over a given time interval is short compared to the first time periods.

In each of the given time intervals, the frequency with which the electrical output from the sensor exceeds a predetermined threshold is determined and that frequency value is stored in a memory for subsequent read-out. The steps of determining the frequency that the sensor output(s) exceeds the predetermined threshold and the storing of the frequency values is repeated for the number of instances defined in the protocol and when all of the instances have been accommodated, an average of all of the frequency values is calculated and stored as an activity log. By performing the foregoing steps for each of the modes established in the protocol, the physician, upon read-out of the stored activity log data, is able to assess the efficacy of the pacing mode changes on patient wellbeing.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which.

DESCRIPTION OF THE PREFERRED EMBODIMENT

The present invention provides a method and an apparatus for assessing the impact on the well being of patients suffering from CHF who are being treated by electrical stimulation of cardiac tissue. In particular, means are provided for evaluating the effect on a patient of a change in the mode of pacing on his/her ability to carry out normal daily activity functions, leading to a programming of the pacemaker at a particular mode that provides maximal benefit. The algorithm to be described herein may also be used to assess the efficacy of different rate responsive sensors or different forms of any single sensor in patients having a rate responsive bradycardia pacemaker implanted.

In implementing the method, an activity sensor is required and it may take a number of forms, such as a respiratory-based sensor for measuring minute ventilation or oxygen up-take, a ECG sensor for detecting heart rate variability or an accelerometer for sensing body motion. With no limitation intended, the present invention will be described using an accelerometer-based activity sensor system.

The accelerometer sensor may be an external device taped to the patient's chest wall or, alternatively, may comprise an accelerometer that is built into the pacemaker itself for providing rate adaptability so as to meet the hemodynamic demands of the body for a given level of activity.

Figure 5:
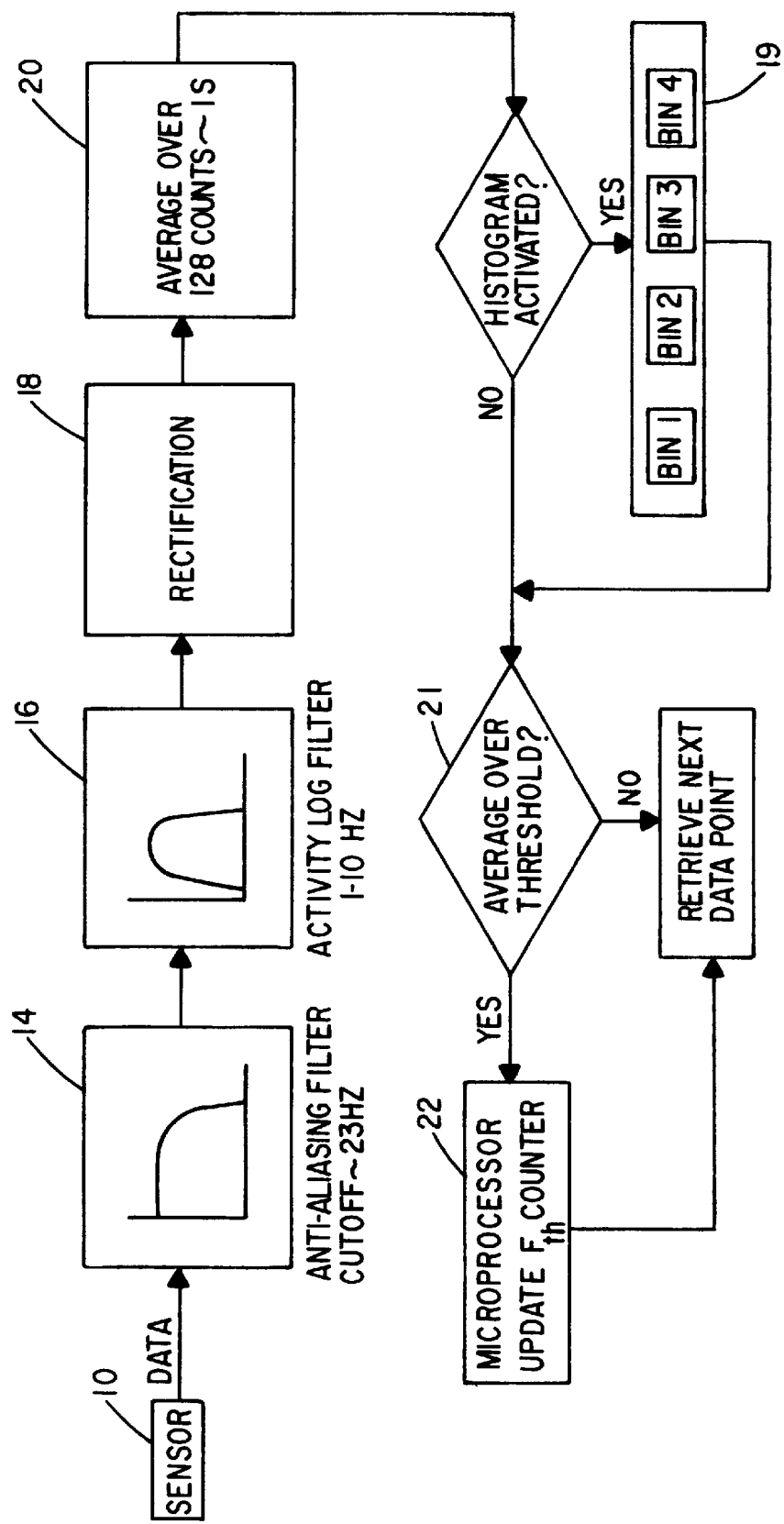
FIG. 5 is a block diagram of the circuitry for processing the raw signal coming from the accelerometer.

The sensor (accelerometer) 10 of FIG. 5 may be a piezoelectric or a piezoresistive device and it produces a raw accelerometer output signal on line 12 proportional to body movement. The raw signal may include noise components due to respiratory activity, heartbeat activity and external vibration affecting the patient's body. The raw signal on line 12 may then be sampled at a predetermined rate, e.g., 500 Hz and then low-pass filtered in an anti-alias Filter 14 having a cut-off frequency of about 23 Hz. It is preferably a finite impulse response (FIR) filter that will down sample the applied input signal from about 500 Hz to about 125 Hz. With a cut-off frequency of about 23 Hz, aliasing is greatly attenuated. The output from the anti-alias filter 14 is then applied to activity filter 16, which is configured as a band-pass filter having a lower cut-off frequency of about 1 Hz and an upper cut-off frequency of about 10 Hz. This insures that noise due to heart sounds and respiration will be effectively removed from the accelerometer output. The absolute value of the accelerometer signal is obtained by rectifying the output from the activity filter and rectifier 18.

Next, the output from the rectifier 18 is averaged in circuit 20 over a predetermined number of counts, e.g., 128 counts. At a sampling rate of 125 Hz, the averaging period is about 1024 milliseconds. The averaging of the absolute value of the filtered accelerometer signal serves to eliminate any high frequency noise signals that can contaminate the results.

Where it is desired to store the average values collected, an efficient storage approach is to construct a histogram having a plurality of bins 19 in which could values can be accumulated on the frequency with which average values reach various magnitudes. As an example, bin 1 may be reserved for sensor averages less than 50 mg, bin 2 for 50–100 mg, bin 3 for 100–150 mg and bin 4 for greater than 150 mg.

The output from the averager is then thresholded in a comparator 21 and then applied to a microprocessor 22 that is programmed to execute the algorithm for assessing patient well-being and for optimizing pacing therapy. As will be explained below, the comparator 21 can be implemented in the microprocessor 22 and need not be a separate component or device.

Figure 6:
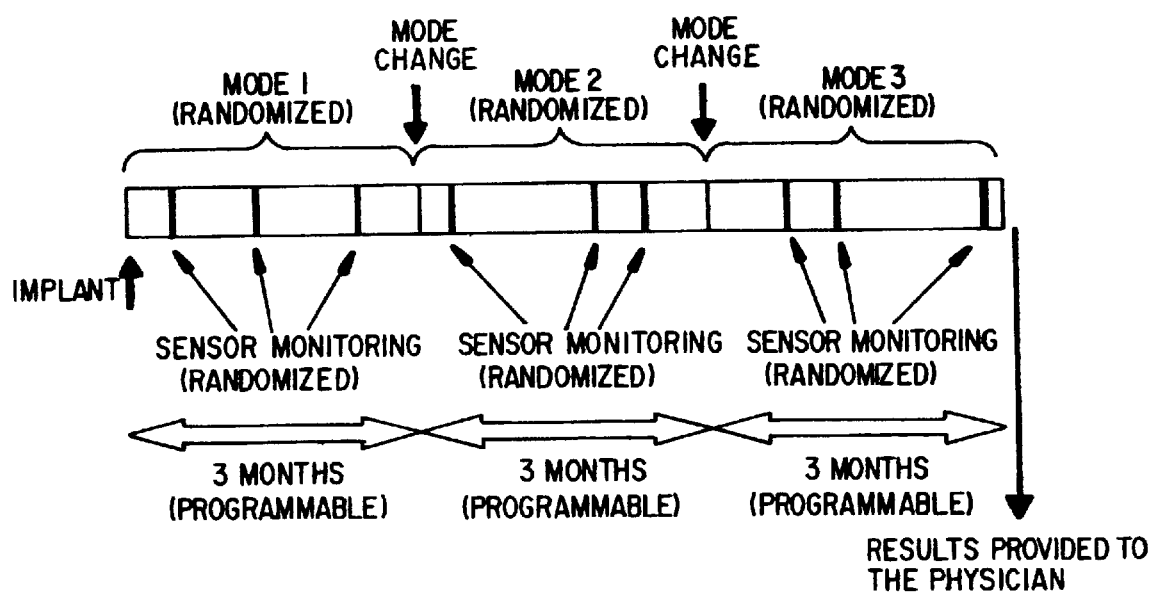
FIG. 6 is a graphical representation helpful in explaining the monitoring protocol employed in carrying out the method of the present invention.

An exemplary monitoring protocol is illustrated graphically in FIG. 6. In this example, the total time period over which the assessment is to be accomplished is nine months, but a longer or shorter total time interval might be used as well. The total time period is shown as being divided into three equal time periods of three months duration. At the time that the patient's pacemaker is implanted, it will be programmed to operate in a first pacing mode (Mode 1) and at the conclusion of the first three month period in which the pacemaker is operating in the first mode, it switches to a second pacing mode (Mode 2). Again, at the conclusion of the second three-month period, the pacemaker is made to operate in a third pacing mode (Mode 3). The term "mode" may refer to a particular pacing parameter, such as lower rate limit, AV delay interval, gain of rate responsive factor of the rate sensor employed, etc. For example, during Mode 1, the lower rate limit may be set at 72 beats-per-minute, in Mode 2 at 80 beats-per-minute and in Mode 3 at 96 beats-per-minute. Alternatively, Mode 1 may involve pacing with a AV delay of 50 milliseconds, Mode 2 at 100 milliseconds, and Mode 3 at 150 milliseconds.

At random times during each of the modes, the activity sensor, i.e., the accelerometer monitoring is enabled for predetermined time intervals that are short compared to the period of time that the pacemaker is operating in a given mode. For example, and as reflected in FIG. 6, the monitoring circuitry may be enabled at three randomly located times within a given three-month period for a period of, say, 24 hours. The suggested 24-hour period is arbitrary and could just as well be 48 hours each, during which patient activity is sensed. It is important that the sensor monitoring times be randomly distributed within each of the modes and that the modes themselves be randomly arranged to avoid bias or skewing of the data due to a patient's own weekly or daily schedules.

Figure 7:
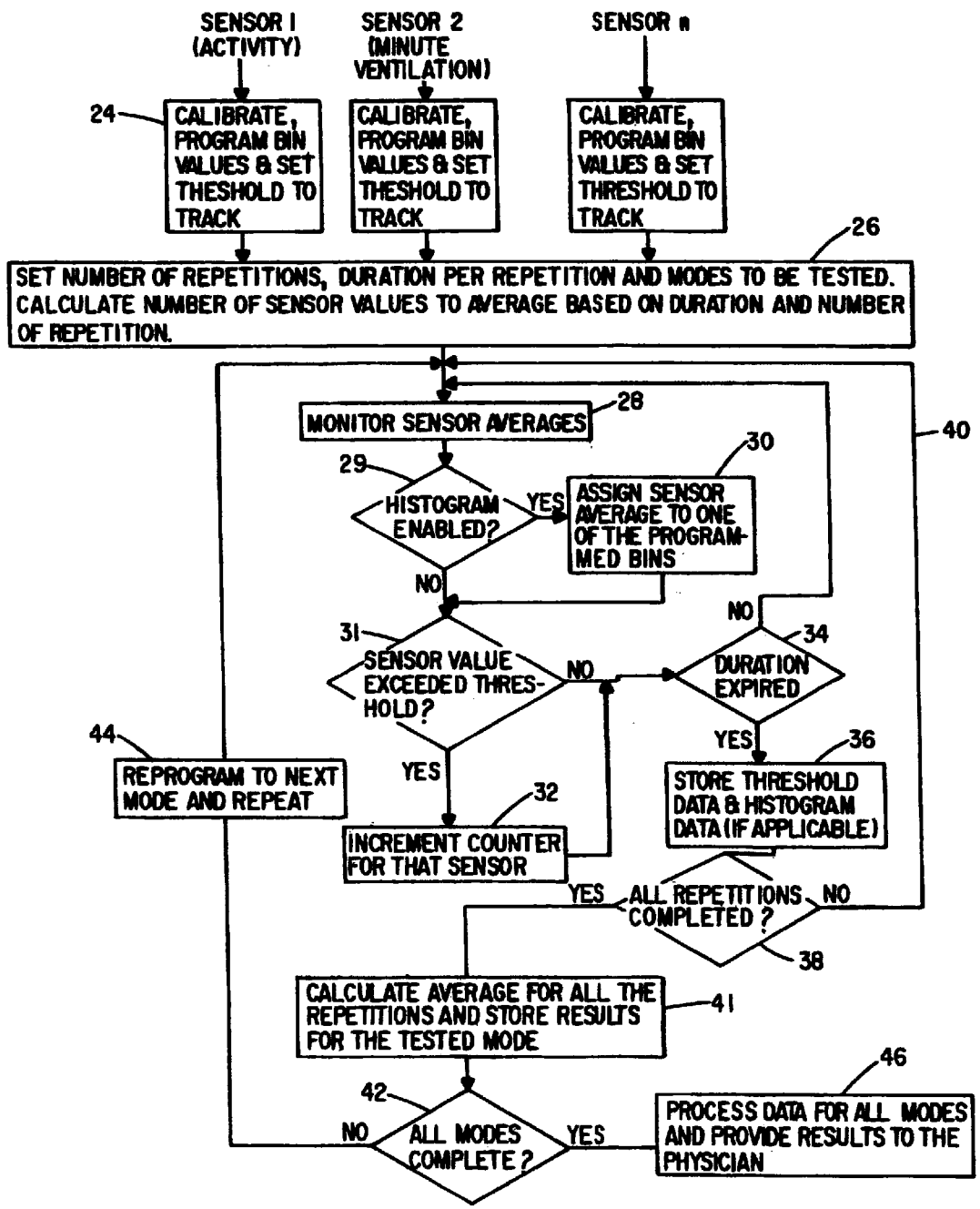
FIG. 7 is a logical flow diagram of the algorithm carried out by the microprocessor-based controller of the FIG. 5.

Referring next to the flow chart of FIG. 7, the algorithm implemented in the microprocessor for collecting data relative to patient well-being or the efficacy or a given pacing mode will now be described. As already mentioned, the invention can be carried out using various types of sensors indicative of patient activity. Illustrated in the flow diagram are a variety of possible choices including an activity sensor, a minute ventilation sensor, a heart rate variability sensor, an oxygen saturation sensor, etc. Typically, one or more sensors can be used in assessing the patient's well-being. As before, for simplicity we will assume that only a single sensor of the accelerometer type is being used for monitoring patient activity (Sensor 1).

The software is initialized by first calibrating and setting a threshold to track (block 24). The threshold may be set by the physician at a predetermined amplitude, such that only those excursions of the accelerometer signal exceeding the threshold will be tallied in a $F_{th}$ counter in microprocessor 22. The threshold would typically be based upon the results obtained by a physician in having the patient perform some sort of a submaximal or maximal exercise and noting the magnitude of the excursions of the sensor (accelerometer) output signals from the averager 20 (FIG. 5). Had multiple sensors been simultaneously utilized, each might have its own threshold. For example, 50 mg may be the threshold for the accelerometer while 100 mg may correlate well with peak $VO_2$, an index of maximal exercise capacity. When tracking multiple clinical parameters that reflect patient well-being, using multiple thresholds, the physician will assign priority ratings for each of the indices being tracked, thus allowing the pacemaker to automatically change therapy, i.e., pacing modes, based on the index assigned the highest priority.

Also as a part of the initialization, the physician will set the number of repetitions that the sensor circuit will be enabled during a given pacing mode, the duration of each such repetition and the pacing modes to be tested.

To conserve memory, it has been found expedient to establish a limit on the number of sensor values to be averaged, and this is based upon the number of repetitions within a given pacing mode period that the sensor is enabled and on the duration for which the sensor is enabled during each repetition. (See block 26.)

A test is made at decision block 29 whether the histogram data collection feature of the pacemaker is enabled and, if so, a sensor average is assigned to one of the programmed bins (block 30). Those skilled in the art desiring more information on histogram data collection and storage in implantable pacers may refer to the Physician's Manual for the VIGOR® pacemaker available from the Guidant Corporation.

With the software running, a time will arrive during the period that the pacemaker is operating in Mode 1 where the output from the averager 20 of FIG. 5 is enabled so that the sensor averages can be monitored (block 28). A determination is made at decision block 31 of FIG. 7 as to whether the sensor averaged signal exceeds the preprogrammed threshold value and, if so, that incident is tallied in a counter (block 32). If the sensor value fails to exceed the threshold, a test is made at decision block 34 to determine whether the time that the sensor circuitry is enabled has elapsed. If not, control passes back to the input of block 28 such that on repeated iterations of that loop an activity log comprising a tally of the frequency with which the sensor value exceeds the threshold is accumulated for the duration of the particular repetition involved, e.g., 24 hours. When that duration expires, the threshold count value for that sensor is stored along with histogram data (block 36).

Next, as reflected at decision block 38, a test is made to determine whether all of the repetitions that are to take place within a given mode period have been completed and, if not, control passes over line 40 back to the input of block 28 and a tally is accumulated of the number of instances during the current repetition that the sensor output exceeds the threshold. Once the test at decision block 38 confirms that all of the repetitions for a given mode of pacing have been completed, the microprocessor calculates an average for all of the repetitions and stores the results for that particular mode. (See block 41.)

Next, a test is made at decision block 42 to determine whether pacing has been completed in all of the assigned modes and, if not, the pacemaker is made to automatically switch to the next mode (block 44) and the above-described sequence of operations is repeated until such time as the test at decision block 42 is affirmative. At that time, the averages for each of the modes as stored at operation block 41 can be tabulated, plotted and provided to the physician for analysis (block 46).

EXAMPLE

Figure 8:
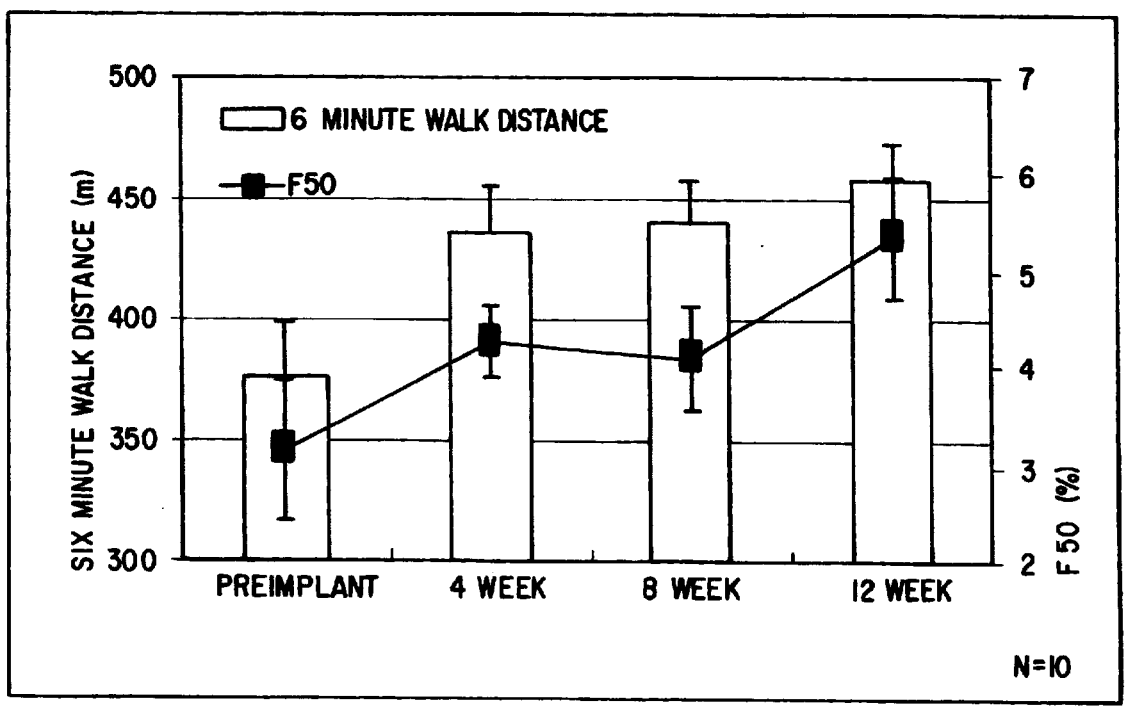
FIG. 8 is a graph showing the relation between changes in the frequency with which the averaged accelerometer output exceeded a 50 mg. threshold ($F_{50}$) with six-minute walk distance for 14 CHF patients receiving pacing therapy.

Investigators at Guidant Corporation (applicant's assignee) tested whether acceleration signals can be used to track the well-being of a CHF patient. Activity levels were tracked using accelerometers in fourteen CHF patients before and after pacemaker implant. At implant, the mean age and NYHA class was 62.2 years and 3.14, respectively. Signals were collected from an accelerometer taped to the skin of the patients. Twenty-four hour data was collected at four time points during a period of 12 weeks: Before pacemaker implant; at the end of four weeks of pacing (4 Wks.); at the end of four weeks of no pacing (8 Wks.); and at the end of four weeks of pacing (12 Wks.). At each of these time points, the patients also underwent a six-minute walk exercise test. The acceleration signals were bandpass filtered at 1–10 Hz, and averaged over a period of one second. Based on the 24-hour profile, the frequency at which the acceleration average exceeded a 50 mg ($F_{50}$) threshold was computed. In two patients, data at four weeks was corrupted due to noise and, hence, eliminated. The graph of FIG. 8 illustrates the results. Compared with pre-implant data, the change in $F_{50}$ correlated significantly ($P<0.05$) with the change in six-minute walk distance. "Sensitivity", defined as the proportion of increases in six minute walk distance identified by an increase in $F_{50}$, was 96.8%. "Specificity", defined as the proportion of decrease in six minute walk distance identified by a decrease in $F_{50}$, was 80%.

Figure 1:
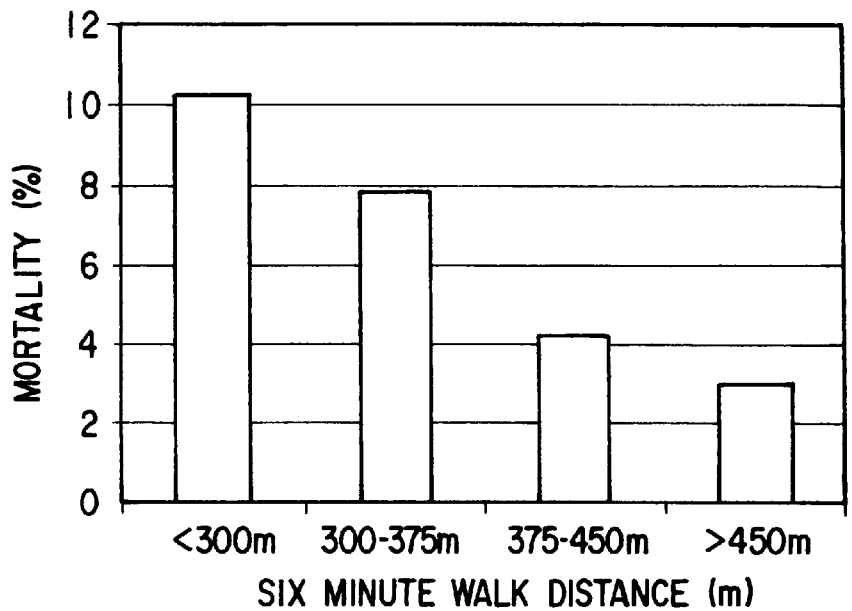
FIG. 1 is a bar graph plotting mortality rates of 898 individual patients considered in a study by Bittner, et al. as a function of distance traversed in a six-minute walk by such patients.
Figure 2:
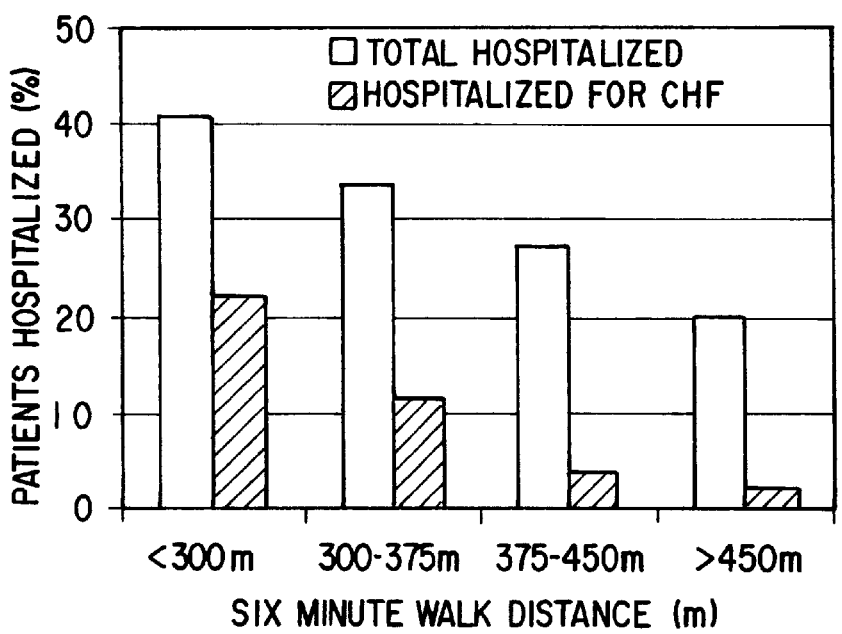
FIG. 2 is a similar bar graph plotting hospitalization rates for such patients.
Figure 3:
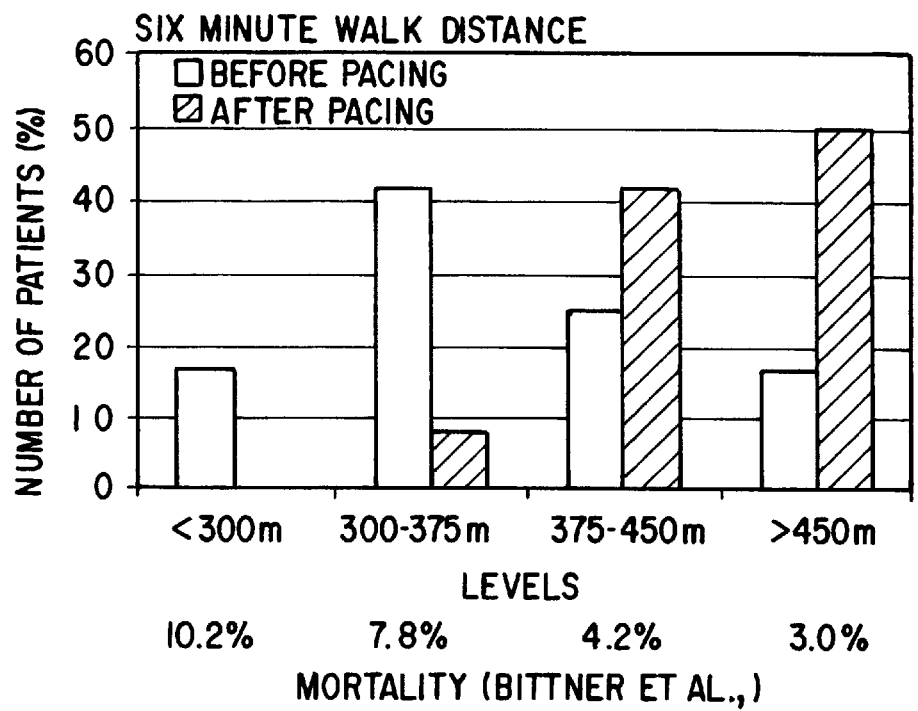
FIG. 3 is a bar graph showing improvement in CHF patient well being measured by six minute walk distance as a result of pacing therapy.
Figure 4:
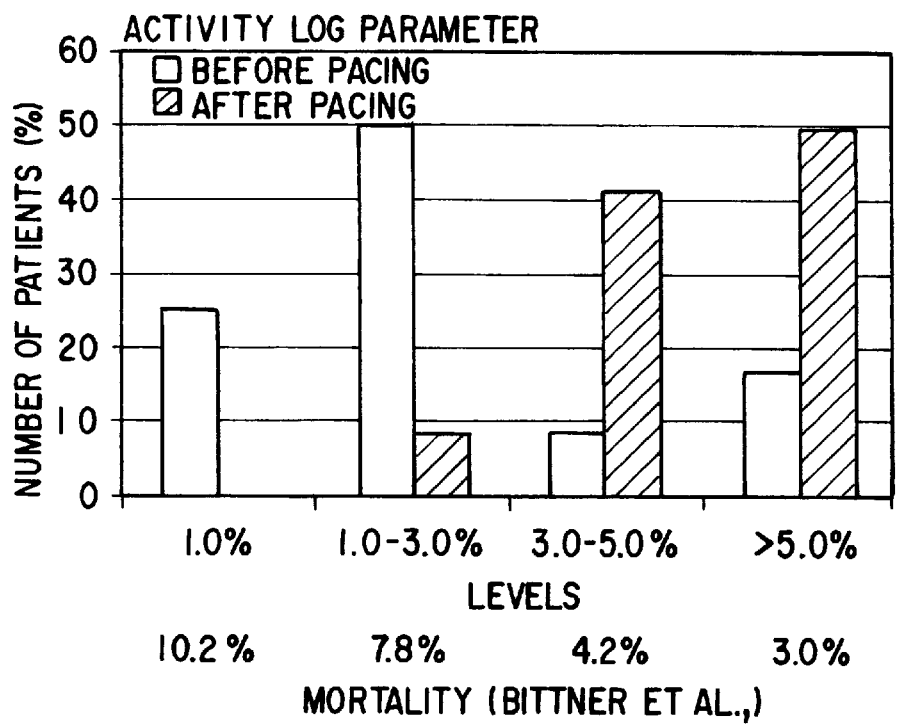
FIG. 4 is a bar graph that shows the improvement in CHF patient well being measured by the frequency parameter derived from the accelerometer.

To assess the change in well being observed with pacing therapy, the patients were classified into four groups based on their six-minute distance performances, as suggested by Bittner, et al., supra. The results are shown in FIG. 3. When compared with pre-implant values (before pacing), there was a right shift in the six-minute walk distance 12 weeks (after pacing). Viewing this data along with the mortality data, also published by Bittner, et al., suggests that the mortality rate may be lowered by pacing therapy. As shown in the bar graph of FIG. 4, the activity log parameter $F_{50}$, can also be used in lieu of the six-minute walk distance to predict changes in mortality.

The mean (+1 STD) of the six-minute walk distance and $F_{50}$ value in seven patients is shown in FIG. 8. Compared with pre-implant values, at 12 weeks, both the six-minute walk distance and $F_{50}$ were significantly different. As a result, we conclude that it is possible to assess the patient's six-minute walk exercise response by tracking acceleration level of the patient, using $F_{50}$. Since it is well established that the distance traveled by a patient in a six-minute walk is a good indicator of a patient's well-being, it follows that the above-described monitoring method can also reliably indicate the beneficial effects of selected therapies on a patient's ability to carry out routine daily activities.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, rather than developing an activity log of the frequency with which a sensor output exceeds a predetermined threshold level during predetermined sampling periods to assess the efficacy of a particular pacing mode on the patient's well-being, the log information can be used for a variety of other purposes. It can be considered by a physician in deciding how to reprogram the AV delay parameter of the patient's pacemaker or it can operate in a closed-loop fashion to automatically optimize the AV delay setting of the pacemaker. The activity log data may also be used in establishing an appropriate interventricular delay for a biventricular pacemaker. That is, a change can be made to the interventricular delay and then the data logging apparatus and method described herein can be used to determine whether such a change proves beneficial. If so, the process can be repeated until a degradation in patient well-being is detected. At this point, the optimum interventricular delay is established.

Still additional decisions can be based upon the outcome of the activity logging technique. For example, if a pacing lead for stimulating the left ventricle has a plurality of switch-selectable electrodes along the length thereof for contacting heart tissue at selected sites on the myocardial surface, the activity log information can be used to determine the particular site that offers the greatest improvement in patient well-being.

What is claimed is:

1. An apparatus for monitoring a patient for assessing patient well-being comprising:
    (a) means for sensing a physiologic parameter of a patient indicative of physical activity and producing an electrical signal proportional thereto;
    (b) means for comparing the electrical signal to a predetermined threshold;
    (c) means for tallying the number of instances in which the electrical signal exceeds the predetermined threshold in a given time interval; and
    (d) means for storing tally-related information for subsequent readout.

2. The apparatus of claim 1 wherein the means for sensing includes an accelerometer.

3. The apparatus of claim 2 and further including signal processing means coupled to receive a raw accelerometer output signal for producing a filtered rectified average of the raw accelerometer signal over a predetermined period as said electrical signal.

4. The apparatus of claim 3 and further including means for recording the filtered rectified average of the raw accelerometer signal.

5. The apparatus of claim 4 wherein the filtered rectified average of the raw accelerometer signal is recorded as a histogram.

6. The apparatus of claim 1 wherein the means for tallying comprises a microprocessor.

7. The apparatus of claim 6 wherein the microprocessor is programmed to sample the electrical signal and compare same to the threshold at random times within a first predetermined time interval, the first predetermined time interval being long relative to a period over which the samples are taken.

8. The apparatus of claim 1 and further including means for presenting the stored tally related information in human readable form.

9. The apparatus of claim 7 wherein the microprocessor is programmed to compute an average of the tallies obtained in the first predetermined time interval.

10. An apparatus for monitoring a patient for assessing the patient's well-being, comprising:
    (a) a physiologic sensor affixed to the patient, the sensor producing an electrical signal proportional to the patient's level of activity;
    (b) a programmed microprocessor coupled to the physiologic sensor for comparing the electrical signal to a predetermined threshold during a plurality of sampling intervals randomly distributed within a time period that is relatively long compared to the sampling intervals, the microprocessor including a memory for storing the electrical signals therein and a counter for tallying the number of occurrences during the sampling intervals that the electrical signals exceed the predetermined threshold; and
    (c) a display device operatively coupled to the microprocessor for presenting tally related information in human perceptible form.

11. The apparatus of claim 10 wherein the physiologic sensor includes an accelerometer.

12. The apparatus of claim 11 and further including signal processing means coupled to receive a raw accelerometer output signal from the accelerometer for producing a filtered, rectified, average of the raw accelerometer signal over a predetermined period as said electrical signal.

13. The apparatus of claim 10 wherein the electrical signals are stored in the memory as a histogram.

* * * * *